(12) United States Patent
Mach et al.

(10) Patent No.: US 6,733,989 B1
(45) Date of Patent: May 11, 2004

(54) STRUCTURAL PHOSPHOPROTEIN (PP28) OF HUMAN CYTOMEGALOVIRUS (HCMV), THE PREPARATION AND USE THEREOF

(75) Inventors: Michael Mach, Erlangen (DE); Heidi Meyer, Spardorf (DE); Michael Bröker, Marburg (DE); Leander Lauffer, Boston, MA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/460,715

(22) Filed: Jun. 2, 1995

Related U.S. Application Data

(62) Division of application No. 07/746,161, filed on Aug. 14, 1991, now abandoned, which is a continuation of application No. 07/313,553, filed on Feb. 22, 1989, now abandoned.

(30) Foreign Application Priority Data

Feb. 24, 1988 (DE) .......................................... 38 05 717

(51) Int. Cl.$^7$ ............................................... C12N 15/38
(52) U.S. Cl. .................. 435/69.1; 435/71.1; 435/252.8; 435/320.1; 435/371; 530/350; 530/352; 530/403; 536/23.1; 536/23.72
(58) Field of Search ............................. 435/69.1, 71.1, 435/252.8, 320.1, 371, 69.3, 71.2; 530/350, 352, 403, 395; 536/23.1, 23.72

(56) References Cited

U.S. PATENT DOCUMENTS 4,727,028 A    2/1988   Santerri et al. ............ 435/240.2

FOREIGN PATENT DOCUMENTS

DE        0268014        6/1987

OTHER PUBLICATIONS

Nowak et al. "Physical mapping of Human Cytomegalovirus Genes: Identification of DNA sequences coding for a virion phosphoprotein of 71 kDa and a viral 65–kDa polypeptide". Virology. Vol. 134, pp 91–102, 1984.*

Meyer et al. "Identification and prokaryotic expression of the gene coding for the highly immunogenic 28–kilodalton structural phosphoprotein (pp28) of human cytomegalovirus". Journal of Virology. Vol. 62, No. 7, pp 2243–2250, Jul. 1988.*

Ihara et al., Cleavage Maps of Human Cytomegalovirus Genome (Strain Towne) Determined by the Use of Cosmid Cloning System. Archives of Virology 88:241–250, 1986.

G. Jahn et al., J. Virol. 67:1358–1367 (1987).

S. Michelson et al., J. Gen. Virol. 70:673–684 (1989).

Allen et al., J. of Virol. 61(8):2454–2461 (1987).

Yew et al., Proc. Natl. Acad. Science, 84:1035–1039 (1987).

Wewer et al., Proc. Natl. Acad. Science, 83:7137–7141 (1986).

Iwasaki et al., J. Biochem. 102:1261–1273 (1987).

Burns et al., Proc. Natl. Acad. Science, 85:602–606 (1988).

Roby, C. and Gibson, W., J. Virol. 59:714–727 (1986).

Nowak, B. et al., Virol. 132(2):325–338 (1984).

Pereira et al., Virol. 139:73–86 (1984).

Irmiere, A. and Gibson, W., J. Gen. Virol. 66:2507–2511 (1985).

Re, M.C. et al., J. Gen. Virol. 66(11):2507–2511 (1985).

Young, R. and Davis, R.W., Proc. Natl. Acad. Sci. USA 80:1194–1198 (1983).

Fleckenstein, B. et al., Gene 18:39–46 (1982).

Stanley, K and Luzio, J.P., EMBO J. 3:1429–1434 (1984).

Hopp, P and Woods, K.R., Proc. Natl. Acad. Sci. USA 81:3824–3828 (1981).

Sofer et al., Bio Techniques, Nov./Dec., 198–203 (1983).

Hutchinson et al., Virology 155(1):172–182 (1986).

Hermiston et al., J. Virol. 61(10):3214–3221 (1987).

Landini et al., J. Med. Virol. 17(4):303–311, (1985).

Irmiere et al., J. Virol. 56(1):277–283 (1985).

* cited by examiner

*Primary Examiner*—Donna C. Wortman
(74) *Attorney, Agent, or Firm*—Finnegan, Henderson, Farabow, Garrett and Dunner, L.L.P.

(57) ABSTRACT

Structural phosphoprotein (pp28) of human cytomegalovirus (HCMV), the preparation and use thereof Expression of an SmaI fragment, which is about 1.0 kb in size, on the left-hand end of the HindIII R fragment makes it possible to synthesize, by genetic manipulation, a structural phosphoprotein of HCMV. This phosphoprotein, or immunogenic parts thereof, can be used as diagnostic aid or vaccine.

36 Claims, 1 Drawing Sheet

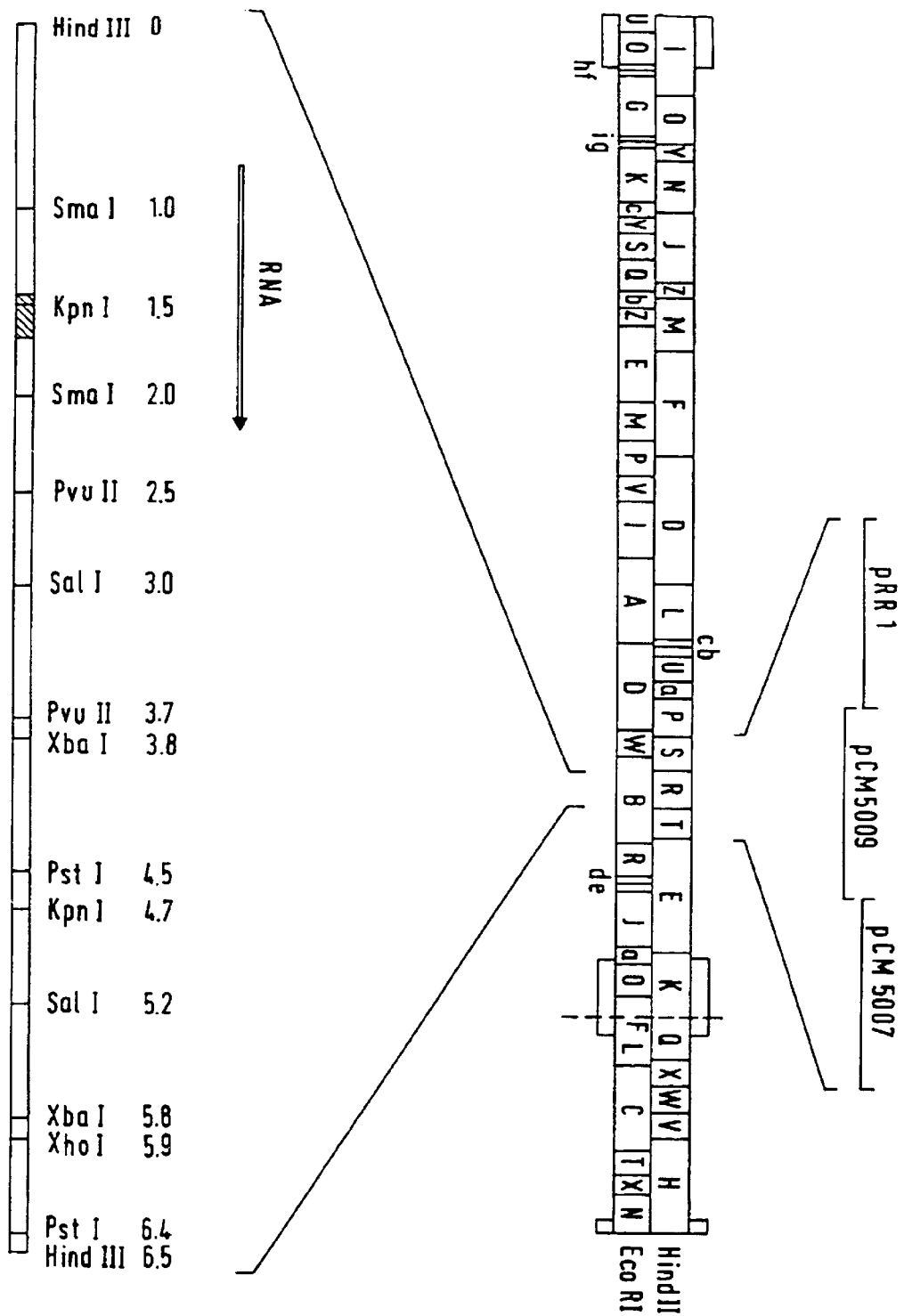

STRUCTURAL PHOSPHOPROTEIN (PP28) OF HUMAN CYTOMEGALOVIRUS (HCMV), THE PREPARATION AND USE THEREOF

This application is a divisional of application Ser. No. 07/746,161, filed Aug. 14, 1991, abandoned, which is a continuation of application Ser. No. 07/313,553, filed Feb. 22, 1989, abandoned.

Structural phosphoprotein (pp28) of human cytomegalovirus (HCMV), the preparation and use thereof The invention relates to a structural HCMV phosphoprotein of 28 kD (pp28) and immunogenic parts thereof, to the preparation thereof by genetic manipulation, and to the use thereof as a diagnostic aid and for producing antibodies and vaccines.

To date, HCMV polypeptides with molecular weights of about 28 kD have been described in several investigations. Roby and Gibson (Roby, C. and Gibson, W. (1986) J. Virol. 59, 714–727) and Nowak et al. (Nowak, B. et al. (1984) Virology 132, 325–338) describe a phosphoprotein of about 24 kD and 29 kD, respectively. It is suggested in both publications that this protein is localized in the matrix. Pereira et al. (Pereira, L. et al. (1984) Virology 139, 73–86) describe a monoclonal antibody which precipitates from infected cell extracts a 25 kD glycoprotein which belongs to the glycoprotein D complex. Irmiere and Gibson (Irmiere, A. and Gibson, W. (1985) J. Virol. 56, 277–283) have identified a 28 kD protein which was found both in the A and in the B capsid of various HCMV strains. Re et al. (Re, M.C. et al. (1985) J. Gen. Virol. 66, 2507–2511) investigated a 28 kD structural protein using a monoclonal antibody P2G11 (MAb P2G11). It remains unclear whether this was the protein described by Pereira et al. (loc. cit.) or that described by Nowak et al. (loc. cit.).

Since a structural protein of 28 kD is recognised by almost all highly positive human sera, and thus the 28 kD proteins must include one of the principal immunogens of HCMV, it appears desirable to identify and to isolate the HCMV gene coding for it. Another aim was subsequently to express this gene in suitable host systems in order to characterize it more accurately and, possibly, to establish it as another principal immunogen of HCMV.

It has been found that it is possible with the MAb P2G11 (Re et al. loc. cit.) to identify and isolate from an HCMV cDNA gene bank clones which code for a 28 kD phosphoprotein (pp28). To date no phosphoprotein 28 kD in size has been disclosed.

BRIEF DESCRIPTION OF THE DRAWING

FIG. 1. Upper part: Physical genome map of HCMV for the restriction endonucleases HindIII and EcoRI. Lower part: Restriction map for the HindIII R fragment. The shaded area shows the region of the cDNA of the clone BUML-1.

To prepare the gene bank, human prepuce fibroblast cells were infected with HCMV, strain Ad 169, and, 96 to 120 hours after the infection, the poly(A)$^+$-RNA was isolated, converted into ds-DNA and, without size fractionation, inserted into the commercially available phage expression vector lambda gt11. For this, the vector was cleaved with EcoRI and treated with alkaline phosphatase (from calf intestine) in order to suppress intramolecular religation. The cDNA was, by attachment of EcoRI linkers, inserted between the phage arms and packaged in vitro. In this way, 100 ng of ds-cDNA resulted in a gene bank which contained about $5 \times 10^5$ independent recombinants and 18% wild-type phages.

The screening of the gene bank was carried out by the method of R. A. Young and R. W. Davis, Proc. Natl. Acad. Sci. USA 80 (1983), 1194–1198, but with the modification that horseradish peroxidase was coupled to protein A, and 4-chloro-1-naphthol was used as detection system, employing the monoclonal antibody P2G11 described above. In this immunoscreening the colonies which are present on nitrocellulose filters are cautiously incubated and, after removal of unbound reactants, positive plaques are detected using the said modified detection system.

On screening of the gene bank with MAb P2G11, two positive signals were obtained from 150,000 recombinant lambda gt11 phages. One clone with an insertion of about 270 base-pairs (bp) was selected and purified for further characterization; it was called BUML-1.

The E.coli strain Y 1089 was infected with the recombinant phage, and the synthesis of the β-galactosidase fusion protein was induced by addition of isopropylthiogalactoside (IPTG). This resulted in the formation of a fusion protein of about 130 kD, which is distinctly larger than the β-galactosidase (118 kD) and is not found in E. coli cells infected with lambda gt11; nor is it present in cells infected with BUML-1 but not induced. In Western blot analyses only the 130 kD polypeptide reacted with MAb P2G11. Hence it is evident that the recombinant clone BUML-1 synthesizes a fusion protein containing a HCMV protein portion.

The cDNA insertion of about 270 bp was now used to locate the gene for the HCMV protein in the viral genome: for this purpose, the abovementioned cDNA insertion was hybridized with 8 cosmid clones which cover the entire genome of HCMV (B. Fleckenstein et al. (1982) Gene 18, 39–46). The cosmid pCM 1058, which contains the HindIII fragments P, R and S, hybridized with the cDNA. More detailed Southern blot analysis of this region localized the HCMV DNA fragment to a 500 bp KpnI/SmaI fragment on the left-hand end of the HindIII R fragment (FIG. 1). It was possible, using an SstII cleavage site, to assign the cDNA to the right-hand KpnI/SmaI fragment in the genome orientation as shown in FIG. 1.

In Northern blot analyses the cDNA fragment of BUML-1 hybridized most strongly with a late mRNA which is 1.3 kb in size and is completely transcribed from the direction of the HindIII R fragment.

10 of 14 HCMV-positive sera selected at random reacted with p28 derived from purified viruses; the same sera likewise reacted with a fusion protein (p271, see Example 1) synthesized by a manipulated gene. When HCMV particles were phosphorylated in vitro (phosphorylated in analogy to Roley, C. and Gibson, W. loc. cit.) it was possible to precipitate a phosphorylated p28 both with MAb P2G11 and with antibodies against the fusion protein p271 (see Example 1). This indicates that the cloned protein is phosphorylated and thus may be called pp28.

Since it would be possible to isolate pp28 in the quantities necessary for diagnostic aids and vaccines only with great technical elaboration, the mode of preparation by genetic manipulation according to the invention is particularly advantageous. It has emerged that not only products expressed by eukaryotic cells but also expression products of bacteria have antigenic activity. Since bacteria do not produce phosphoproteins from foreign genes, it was not to be expected that "HCMV pp28", or parts thereof, prepared in bacteria would also have strong immunogenic activity. However, it has emerged that even such proteins are just as unambiguously recognized by appropriate sera as is authentic pp28.

Consequently, the invention relates to a) the purified and isolated DNA sequence of the KpnI/SmaI fragment on the left-hand end of the HindIII R fragment of HCMV as shown in FIG. 1, including the transcription products thereof, b) DNA structures and vectors containing this sequence in whole or in part, c) pro- or eukaryotic cells transformed with such DNA, d) the polypeptides, or parts thereof, expressed by these cells by reason of the transformation, e) the amino acid sequences thereof, and the use thereof as a diagnostic aid, f) antibodies against the polypeptides in section d), including the use thereof for passive immunization, for diagnosis and for purifying said polypeptides, g) vaccines against HCMV, which contain peptides and amino acid sequences from (e) alone or in combination, h) and a method for the preparation, by genetic manipulation, of the polypeptides, or parts thereof, mentioned in section (d).

Further embodiments of the invention are defined in the examples which follow and in the patent claims.

EXAMPLE 1

Construction and Expression of the Plasmid p271

Firstly, the plasmid pHM 7 was produced by inserting the approximately 500 bp KpnI-SmaI fragment into M13mp11. The plasmid p271 is obtained by insertion of the approximately 500 bp EcoRI-SmaI fragment of pHM 7 into pEX-2 (Stanley, K. and P. Luzio (1984) EMBO Journal 3, 1429–1434). Insertion into pEX 1 and pEX 3 produced no fusion proteins. The plasmid p271 thus codes for a fusion protein of about 133 kD, composed of a pp28 portion (about 18 kD) fused to a Cro/β-galactosidase hybrid protein (about 115 kD). Expression in suitable E. coli strains is induced by heat-inactivation of a temperature-sensitive repressor. E.coli pop 2136 (Stanley, K. and P. Luzio loc. cit.) was cultured to a density of 0.2–0.3 ($A_{600}$ nm) at 30° C., and the synthesis of the fusion protein was induced by a rapid change in temperature to 42° C. After 90 min at 42° C., the cells were harvested, and the pp28 protein was purified by known methods. The fusion protein contributes about 5% of the total protein mass.

EXAMPLE 2

Optimization of pp28 Expression

By the reclonings described hereinafter it was possible (1) to improv overall the expression of pp28 as a fusion protein and (2) to reduce the foreign portion in the fusion protein. The starting plasmid chosen was pBD2IC20H (European Patent Application EP 0,236,978). This plasmid thus codes for a β-galactosidase portion which is considerably (by more than 60%) shorter than with pEX-2, and induction was effected via the lac promoter system by addition of isopropylthiogalactoside (IPTG).

Two strategies were chosen for the cloning of the pp28 DNA fragment from p271:

1) p271 was cut with EcoRI and SmaI, and the EcoRI protrusions were filled in using the Klenow fragment. The resulting approximately 500 bp fragment was inserted into the SmaI site of pBD2IC20H. The linker region of the resulting plasmid pGB10 has the following DNA sequence (verified by indirect sequencing on the double-strand):

```
    (S) E (filled in)              S
    (m) c                          m
    (a) o                          a
    (I) R                          I
        I
GATGGGGATCCCCAATTCGAGCTCGCCCGACC...CCCGGG
---------+---------+---------ca. 500bp---
CTACCCCTAGGGGTTAAGCTCGAGCGGGCATGG:::GGGCCC
from pBD2IC20H>< from p 271 >< pp28...    >
AspGlyAspProGlnPheGluLeuAlaArgThr...ProGly
```

2) The reading frame in the linker region of pBD2IC20H was shifted by filling in the Bam HI site (→plasmid pGB11). It was then possible for the EcoRI/SmaI fragment from p271 to be inserted, without previous filling-in of the EcoRI site, directly into pGB11 which had been cut with EcoRI and NruI. The linker region of the resulting plasmid pGB12 has the following DNA sequence:

```
                                    E                         (S N)
                                    c                         (m r)
                                    o                         (a u)
                                    R                         (I I)
                                    I
GATGGGGATCGATCCCCGGGTACCGAGCTCGAATTCGAGCTCGCCCGTACC...CCCCGA
---------+---------+---------+---------+-------ca. 500bp----
CTACCCCTAGCTAGGGGCCCATFFCTCGAGCTTAAGCTCGAGCGGGCATGG...GGGGCT
       from pGB11           >< from p271    >< pp28... >
AspGlyAspArgSerProGlyThrGluLeuGluPheGluLeuAlaArgThr...ProArg
```

Estimation of the color intensity of the relevant protein bands after fractionation of E. coli total extracts revealed that the p271-encoded protein, after its induction, made up about 5% of the total protein content, whereas the corresponding figures for pGB10 and PGB12 were throughout about 20%. If account is taken of the fact that the foreign protein content in the pGB10- and pGB12-encoded fusion proteins is less than in that encoded by p271, it is evident that pp28 expression is increased about ten-fold by use of pGB10 or pGB12.

What is claimed is:

1. A prokaryotic expression vector encoding the entire HCMV pp28 that elicits antibodies that immunologically bind to pp28, wherein said vector expresses said entire HCMV pp28 in prokaryotic cells.

2. A method for the preparation of the entire HCMV pp28 which comprises expressing the expression vector which codes for said entire HCMV pp28 as claimed in claim 1.

3. A prokaryotic expression vector encoding an antigenic portion of HCMV pp28 that elicits antibodies that immunologically bind to pp28, wherein said vector expresses said antigenic portion of HCMV pp28 in prokaryotic cells.

4. The prokaryotic expression vector of claim 3, wherein said expression vector is bacteriophage vector.

5. The prokaryotic expression vector of claim 3, wherein said prokaryotic expression vector is a lambda phage vector.

6. The prokaryotic expression vector of claim 3, wherein said prokaryotic expression vector encodes a fusion protein.

7. The prokaryotic expression vector of claim 3, wherein said prokaryotic expression vector comprises a 1.0 kB SmaI/SmaI fragment of HCMV.

8. The prokaryotic expression vector of claim 3, wherein said prokaryotic expression vector comprises a 0.5 kB KpnI/SmaI fragment of HCMV.

9. The prokaryotic expression vector of claim 3, wherein said prokaryotic expression vector comprises a 0.5 kB SmaI/KpnI fragment of HCMV.

10. The prokaryotic expression vector of claim 3, wherein said prokaryotic expression vector comprises a 1.0 kB SmaI/SmaI fragment of HCMV strain Ad 169.

11. The prokaryotic expression vector of claim 3, wherein said prokaryotic expression vector comprises a 0.5 kB KpnI/SmaI fragment of HCMV strain Ad 169.

12. The prokaryotic expression vector of claim 3, wherein said prokaryotic expression vector comprises a 0.5 kB SmaI/KpnI fragment of HCMV strain Ad 169.

13. A method for the preparation of an antigenic portion of HCMV pp28 which comprises expressing the expression vector which codes for said antigenic portion of HCMV pp28 as claimed in claim 3.

14. A prokaryotic cell which is transformed with a recombinant DNA molecule encoding the entire HCMV pp28 that elicits antibodies that immunologically bind to pp28, wherein said cell expresses said entire HCMV pp28.

15. The prokaryotic cell of claim 14, wherein said prokaryotic cell is a bacterium.

16. A prokaryotic cell which is transformed with a recombinant DNA molecule encoding an antigenic portion of HCMV pp28 that elicits antibodies that immunologically bind to pp28, wherein said cell expresses said antigenic portion of HCMV pp28.

17. The prokaryotic cell of claim 16, wherein said prokaryotic cell is a bacterium.

18. The prokaryotic cell of claim 16, wherein said prokaryotic cell is *E. coli*.

19. The prokaryotic cell of claim 16, wherein said DNA molecule comprises a 1.0 kB SmaI/SmaI fragment of HCMV.

20. The prokaryotic cell of claim 16, wherein said DNA molecule comprises a 0.5 kB KpnI/SmaI fragment of HCMV.

21. The prokaryotic cell of claim 16, wherein said DNA molecule comprises a 0.5 kB SmaI/KpnI fragment of HCMV.

22. The prokaryotic cell of claim 16, wherein said DNA molecule comprises a 1.0 kB SmaI/SmaI fragment of HCMV strain Ad 169.

23. The prokaryotic cell of claim 16, wherein said DNA molecule comprises a 0.5 kB KpnI/SmaI fragment of HCMV strain Ad 169.

24. The prokaryotic cell of claim 16, wherein said DNA molecule comprises a 0.5 kB SmaI/KpnI fragment of HCMV strain Ad 169.

25. A eukaryotic cell which is transformed with a recombinant DNA molecule encoding an antigenic portion of HCMV pp28 that elicits antibodies that immunologically bind to pp28, wherein said cell expresses said antigenic portion of HCMV pp28 in said cell.

26. The eukaryotic cell of claim 25, wherein said DNA molecule comprises a 1.0 kB SmaI/SmaI fragment of HCMV.

27. The eukaryotic cell of claim 25, wherein said DNA molecule comprises a 0.5 kB KpnI/SmaI fragment of HCMV.

28. The eukaryotic cell of claim 25, wherein said DNA molecule comprises a 0.5 kB SmaI/KpnI fragment of HCMV.

29. The eukaryotic cell of claim 25, wherein said DNA molecule comprises a 1.0 kB SmaI/SmaI fragment of HCMV strain Ad 169.

30. The eukaryotic cell of claim 25, wherein said DNA molecule comprises a 0.5 kB KpnI/SmaI fragment of HCMV strain Ad 169.

31. The eukaryotic cell of claim 25, wherein said DNA molecule comprises a 0.5 kB SmaI/KpnI fragment of HCMV strain Ad 169.

32. A eukaryotic cell which is transformed with a recombinant DNA molecule encoding the entire HCMV pp28 that elicits antibodies that immunologically bind to pp28, wherein said cell expresses said entire HCMV pp28 in said cell.

33. An isolated 0.5 kB KpnI/SmaI fragment encoding an antigenic portion of HCMV pp28 that elicits antibodies that immunologically bind to pp28.

34. An isolated 1.0 kB SmaI/SmaI fragment encoding an antigenic portion of HCMV pp28 that elicits antibodies that immunologically bind to pp28.

35. An isolated 0.5 kB KpnI/SmaI fragment encoding an antigenic portion of HCMV pp28 strain Ad 169 that elicits antibodies that immunologically bind to pp28.

36. An isolated 1.0 kB SmaI/SmaI fragment encoding an antigenic portion of HCMV pp28 strain Ad 169 that elicits antibodies that immunologically bind to pp28.

* * * * *